United States Patent
Nagamizu et al.

(10) Patent No.: US 8,419,616 B2
(45) Date of Patent: Apr. 16, 2013

(54) IMAGE PICKUP DEVICE WITH A PROTECTION MEMBER AND AN OPTICAL REFLECTION MEMBER

(75) Inventors: Hiroyuki Nagamizu, Sagamihara (JP); Hiroshi Unsai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1294 days.

(21) Appl. No.: 12/182,598

(22) Filed: Jul. 30, 2008

(65) Prior Publication Data
US 2009/0062616 A1   Mar. 5, 2009

(30) Foreign Application Priority Data

Aug. 20, 2007 (JP) .................. 2007-226622

(51) Int. Cl.
- A61B 1/04  (2006.01)
- A61B 1/00  (2006.01)
- H04N 9/07  (2006.01)
- H04N 5/225 (2006.01)
- G02B 5/04  (2006.01)

(52) U.S. Cl.
USPC ........... 600/109; 600/129; 348/337; 348/340; 359/831; 359/833

(58) Field of Classification Search .................. 600/140, 600/175, 121, 173, 109, 129, 130, 176; 606/34, 606/41; 348/65, 337, 340; 359/827, 703, 359/824, 826, 794, 738, 627, 831, 833, 837; 428/220
See application file for complete search history.

(56) References Cited

U.S. PATENT DOCUMENTS

| | | | | |
|---|---|---|---|---|
| 5,221,998 A | * | 6/1993 | Sugahara | 359/831 |
| 5,236,541 A | * | 8/1993 | Sugahara | 156/556 |
| 5,743,610 A | * | 4/1998 | Yajima et al. | 353/31 |
| 5,909,944 A | * | 6/1999 | Yajima et al. | 353/81 |
| 5,910,816 A | * | 6/1999 | Fontenot et al. | 348/65 |
| 6,137,637 A | * | 10/2000 | Ju et al. | 359/678 |

(Continued)

FOREIGN PATENT DOCUMENTS

| GB | 319195 | 9/1929 |
|---|---|---|
| JP | 61-254917 | 11/1986 |

(Continued)

OTHER PUBLICATIONS

Summons to attend oral proceedings pursuant to Rule 115(1) EPC dated Apr. 9, 2010.

*Primary Examiner* — John P Leubecker
*Assistant Examiner* — Ronald D Colque
(74) *Attorney, Agent, or Firm* — Scully Scott Murphy & Presser, PC

(57) ABSTRACT

An image pickup unit according to the present invention, includes a solid-state image pickup device provided with a light receiving portion for receiving photographing light refracted and reflected by a reflection surface of an optical reflection member. The image pickup unit also includes a protection member which is surface-joined to and to protect at least the area of an effective reflection surface within the reflection surface by which the photographing light is refracted and made incident on the light receiving portion. Thereby, when the image pickup unit is provided in an electronic endoscope including the optical component for refracting and reflecting the photographing light, it is possible to improve the assembling property of the image pickup unit including the optical component, and possible to prevent the optical component from being damaged under various environment.

13 Claims, 13 Drawing Sheets

U.S. PATENT DOCUMENTS

| | | | | |
|---|---|---|---|---|
| 6,141,150 | A * | 10/2000 | Ushiyama et al. | 359/618 |
| 6,181,414 | B1 * | 1/2001 | Raz et al. | 356/51 |
| 6,530,882 | B1 * | 3/2003 | Farkas et al. | 600/168 |
| 6,679,839 | B2 * | 1/2004 | Farkas et al. | 600/178 |
| 6,690,521 | B2 * | 2/2004 | Hashizume et al. | 359/831 |
| 6,762,884 | B2 * | 7/2004 | Beystrum et al. | 359/629 |
| 6,949,069 | B2 * | 9/2005 | Farkas et al. | 600/178 |
| 7,114,846 | B2 * | 10/2006 | Tominaga et al. | 374/121 |
| RE39,859 | E * | 9/2007 | Ushiyama et al. | 359/618 |
| 7,417,682 | B2 * | 8/2008 | Kuwakino et al. | 348/345 |
| 7,527,186 | B2 * | 5/2009 | Beatson et al. | 228/4.5 |
| 7,589,923 | B2 * | 9/2009 | Takano et al. | 359/833 |
| 7,762,466 | B2 * | 7/2010 | Tan et al. | 235/462.42 |
| 7,878,662 | B2 * | 2/2011 | Hsu | 353/81 |
| 7,981,230 | B2 * | 7/2011 | Ogawa | 156/99 |
| 8,026,971 | B2 * | 9/2011 | Mitsumine et al. | 348/336 |
| 2002/0021505 | A1 * | 2/2002 | Lee | 359/834 |
| 2002/0057341 | A1 * | 5/2002 | Tanaka | 348/143 |
| 2002/0057496 | A1 * | 5/2002 | Kanai | 359/625 |
| 2002/0171749 | A1 * | 11/2002 | Kamakura et al. | 348/341 |
| 2003/0218952 | A1 * | 11/2003 | Katayama et al. | 369/53.26 |
| 2004/0263616 | A1 * | 12/2004 | Yamaguchi | 348/65 |
| 2005/0259553 | A1 * | 11/2005 | Katayama | 369/112.02 |
| 2006/0098283 | A1 * | 5/2006 | Sato | 359/486 |
| 2007/0115376 | A1 * | 5/2007 | Igarashi | 348/262 |
| 2008/0136946 | A1 * | 6/2008 | Hasegawa | 348/294 |
| 2009/0002857 | A1 * | 1/2009 | Tokunaga et al. | 359/833 |

FOREIGN PATENT DOCUMENTS

| | | |
|---|---|---|
| JP | 62-15514 | 1/1987 |
| JP | 04-317622 | 11/1992 |
| JP | 2000-107120 A | 4/2000 |
| JP | 2000-329912 | 11/2000 |
| JP | 2002-023067 | 1/2002 |
| JP | 2002-291693 A | 10/2002 |
| JP | 2003-116789 A | 4/2003 |
| JP | 2005-221632 A | 8/2005 |
| JP | 2005-309090 | 11/2005 |
| JP | 2005-345933 | 12/2005 |
| JP | 2006-106166 A | 4/2006 |
| JP | 2007-089764 A | 4/2007 |
| JP | 2007-157223 | 6/2007 |
| WO | WO 2007/060835 A1 | 5/2007 |

* cited by examiner

IMAGE PICKUP DEVICE WITH A PROTECTION MEMBER AND AN OPTICAL REFLECTION MEMBER

This application claims benefit of Japanese Application No. 2007-226622 filed on Aug. 31, 2007 the contents of which are incorporated by this reference.

BACKGROUND OF THE INVENTION

1. Field of the Invention

The present invention relates to an image pickup unit, and more particularly to an image pickup unit which is arranged in a distal end portion of an endoscope and which includes an optical reflection member for refracting and reflecting photographing light.

2. Description of the Related Art

In recent years, endoscopes have been widely used in medical fields and industrial fields. The endoscopes include a conventional fiberscope type endoscope for observing an observation image through an eyepiece by using an image fiber, and an electronic endoscope in which a solid-state image pickup device is arranged in an endoscope distal end portion, an endoscope operation portion, or the like, and which displays an observed image in a monitor.

The conventional electronic endoscope includes, as disclosed in, for example, Japanese Patent Application Laid-Open Publication No. 61-254917 and Japanese Patent Application Laid-Open Publication No. 4-317622, a type using a configuration in which, in order to achieve slenderization by effectively using a space in a distal end portion, photographing light is refracted and reflected by a prism in the direction approximately perpendicular to the longitudinal axis of the distal end portion, and in which a light receiving surface of a solid-state image pickup device forming an image of the photographing light, is arranged at a position so as to be in parallel with the longitudinal axis of the distal end portion.

In the conventional image pickup unit, there is arranged a prism holding base, or a reinforcing member brought into contact with or fixed to an inclined surface on which the reflection surfaces of two prisms are formed. The conventional image pickup unit is arranged and fixed in the distal end portion of the endoscope in such a way that the reinforcing member or the prism holding base is fixed to the distal end portion of the endoscope with screws.

SUMMARY OF THE INVENTION

An image pickup unit according to the present invention includes a solid-state image pickup device provided with a light receiving portion which receives photographing light refracted and reflected by a reflection surface of an optical reflection member, and also includes a protection member which is surface-joined to and to protect at least the area of an effective reflection surface within the reflection surface by which the photographing light is refracted and made incident on the light receiving portion.

The above and other objects, features and advantages of the invention will become more clearly understood from the following description referring to the accompanying drawings.

DETAILED DESCRIPTION OF THE PREFERRED EMBODIMENTS

In the following, embodiments according to the present invention will be described with reference to the accompanying drawings. Note that the embodiments according to the present invention will be described below by using an endoscope apparatus which is a medical apparatus and is inserted into a body cavity to observe an organism tissue.

(First Embodiment)

First, there will be described an image pickup unit according to a first embodiment with reference to FIG. 1 to FIG. 8.

Figure 1:
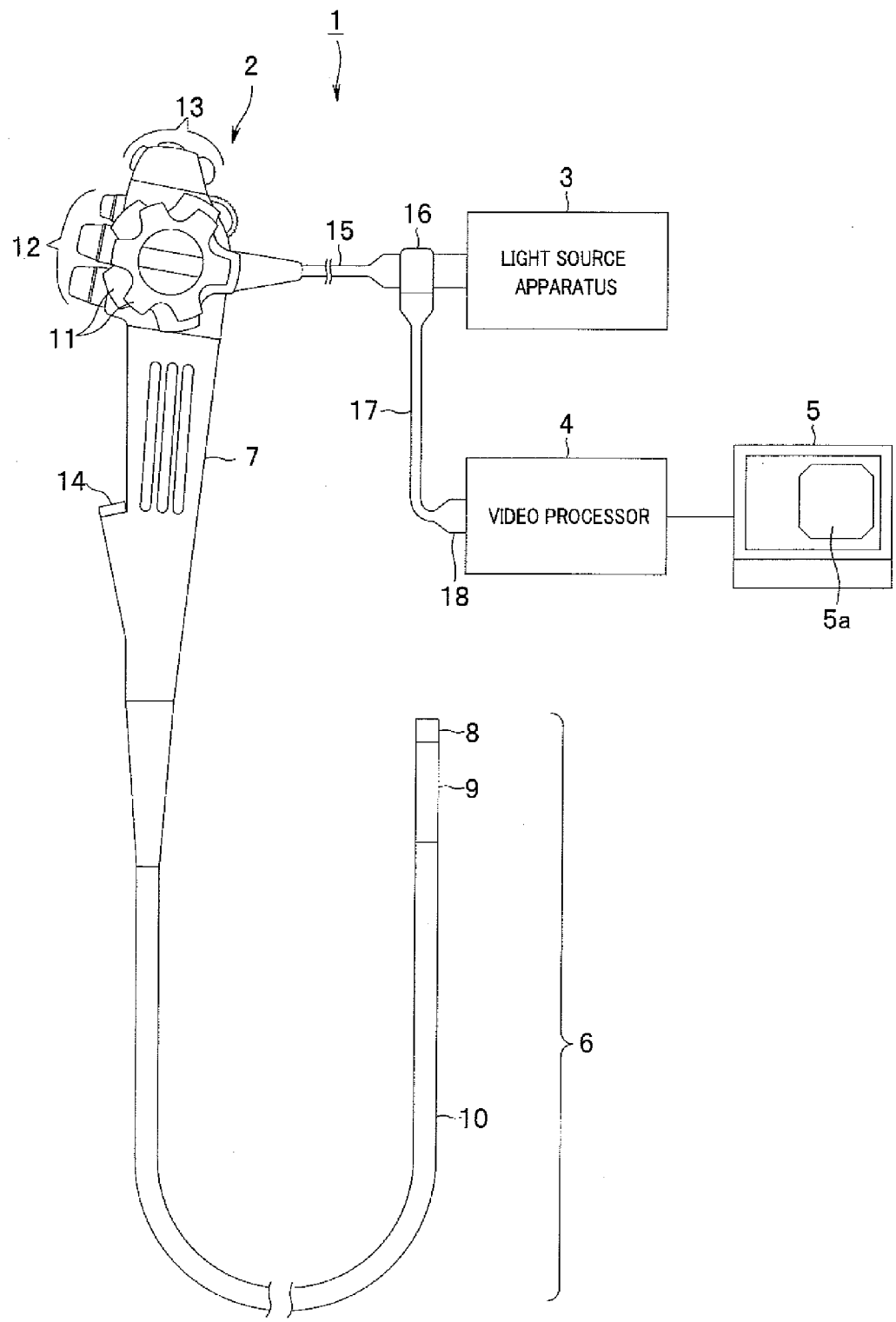
FIG. 1 is a view showing a configuration of an electronic endoscope system according to a first embodiment of the present invention.
Figure 2:
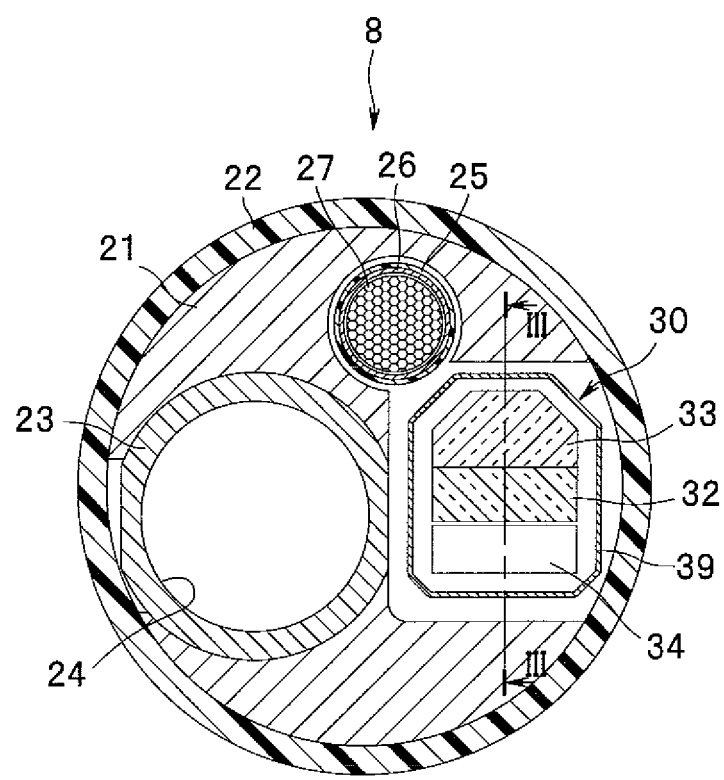
FIG. 2 is a sectional view of a distal end portion of an electronic endoscope of the electronic endoscope system according to the first embodiment of the present invention.
Figure 3:
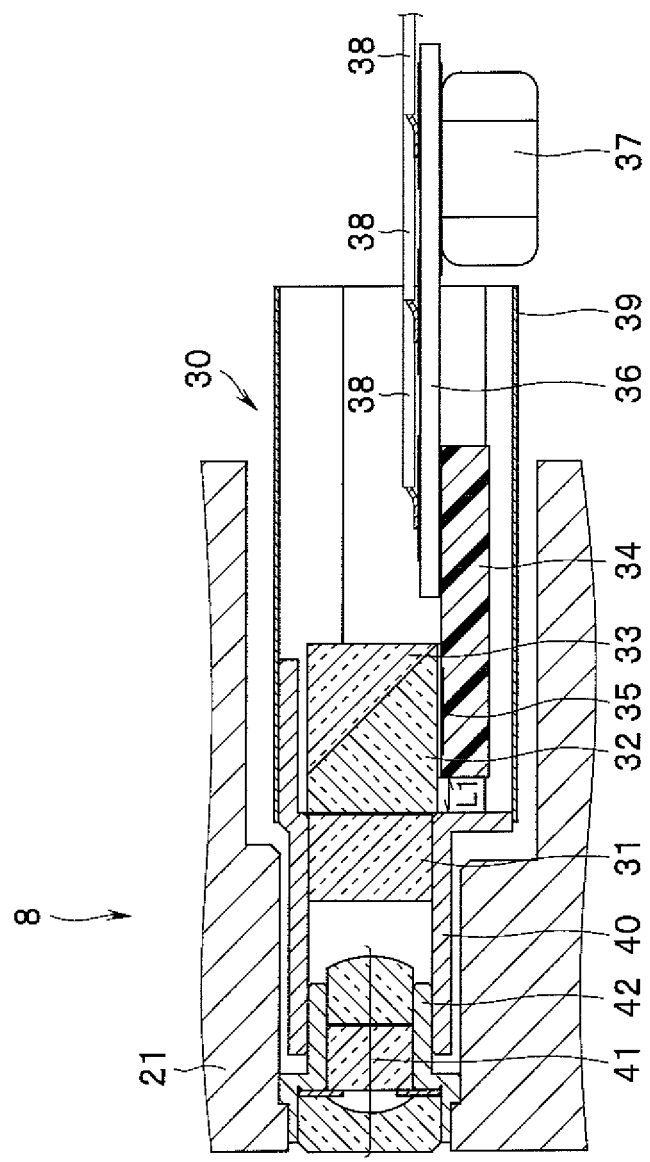
FIG. 3 is a sectional view of the distal end portion of the electronic endoscope along the line III-III in FIG. 2 according to the first embodiment of the present invention.
Figure 4:
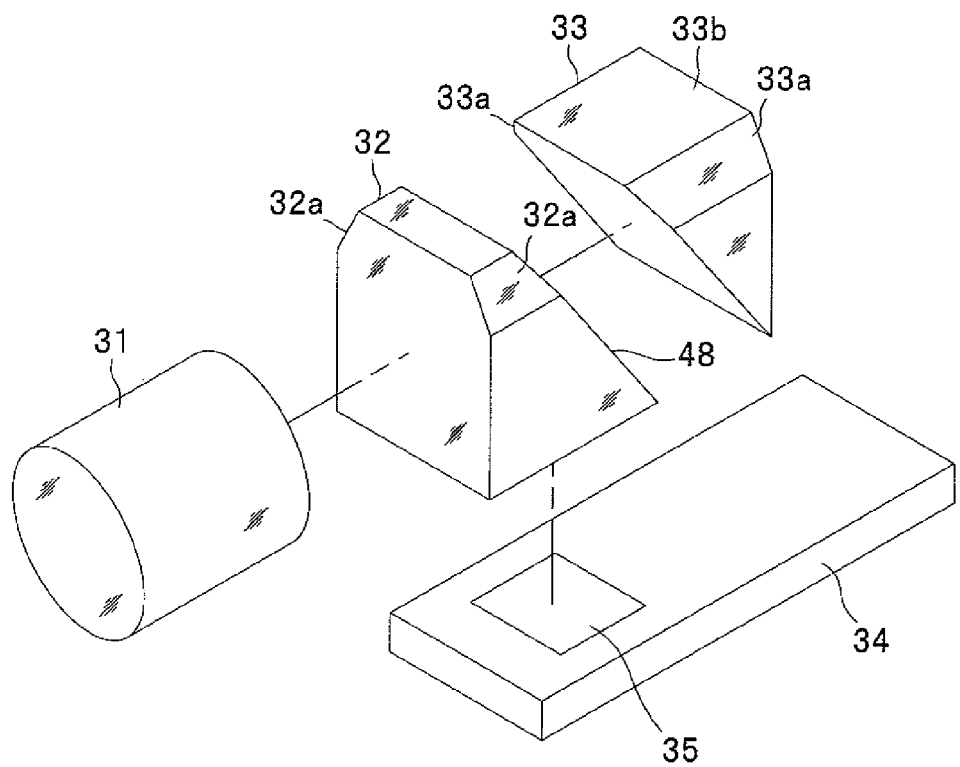
FIG. 4 is an exploded perspective view of an image pickup unit of the electronic endoscope according to the first embodiment of the present invention.
Figure 5:
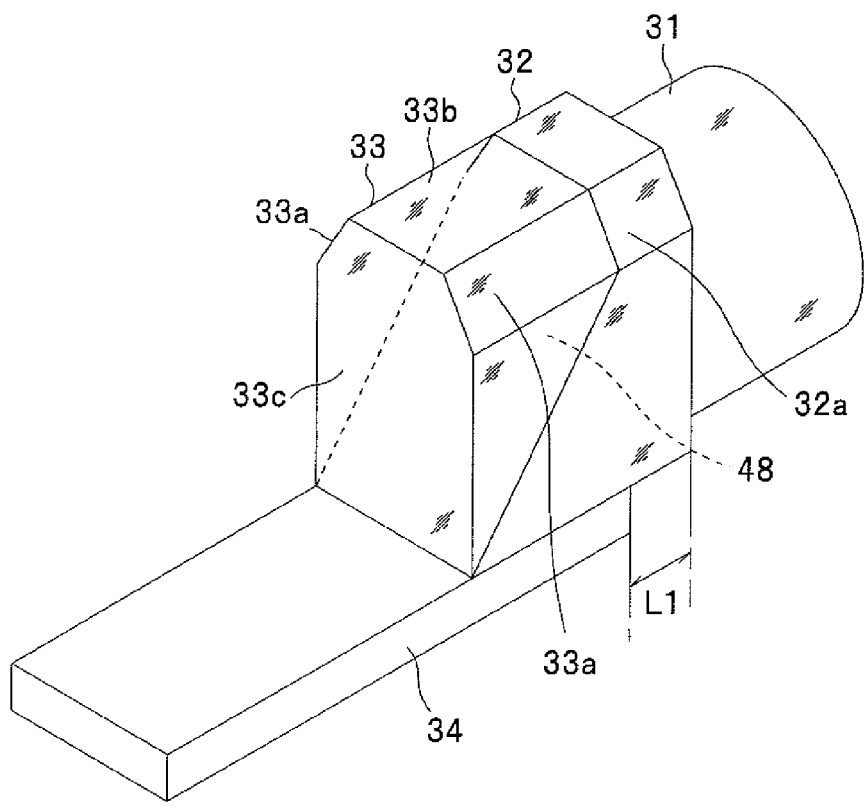
FIG. 5 is a rear right side perspective view of a part of the image pickup unit after being assembled from the state shown in FIG. 4 according to the first embodiment of the present invention.
Figure 6:
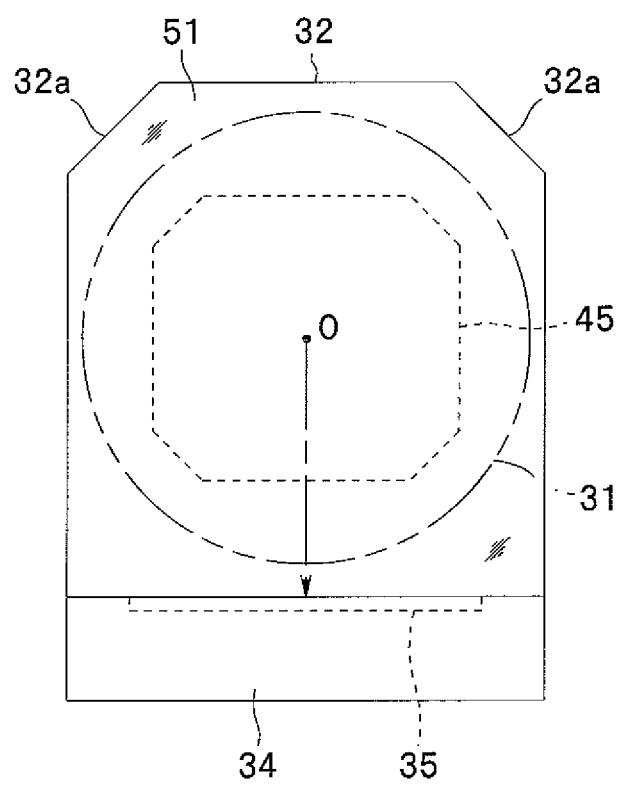
FIG. 6 is a front view of the image pickup unit according to the first embodiment of the present invention.
Figure 7:
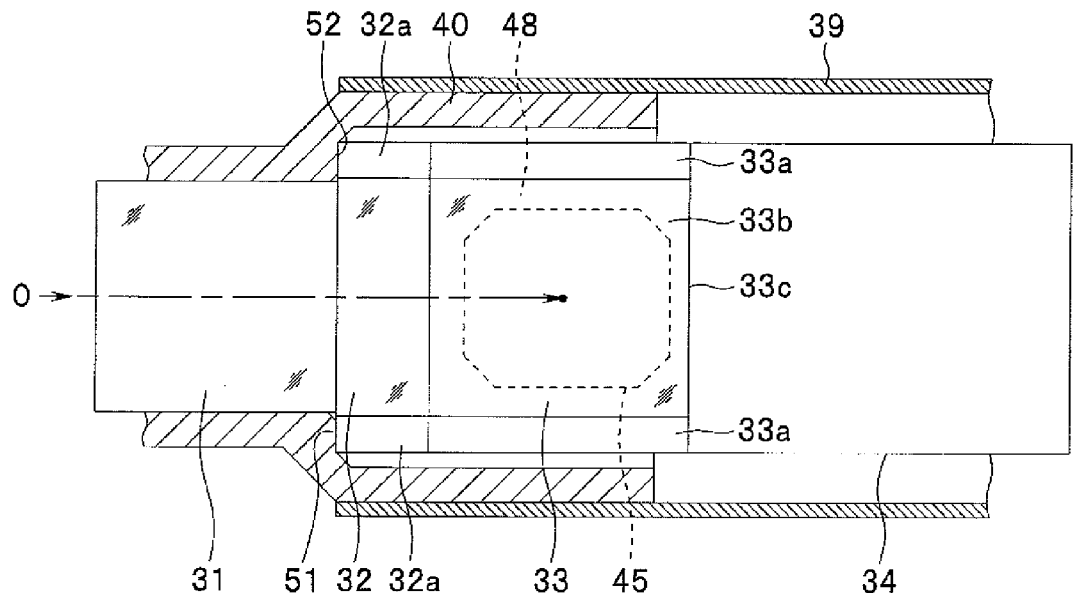
FIG. 7 is a top view showing in cross section a part of the image pickup unit fixed in a lens frame and a reinforcing frame according to the first embodiment of the present invention.
Figure 8:
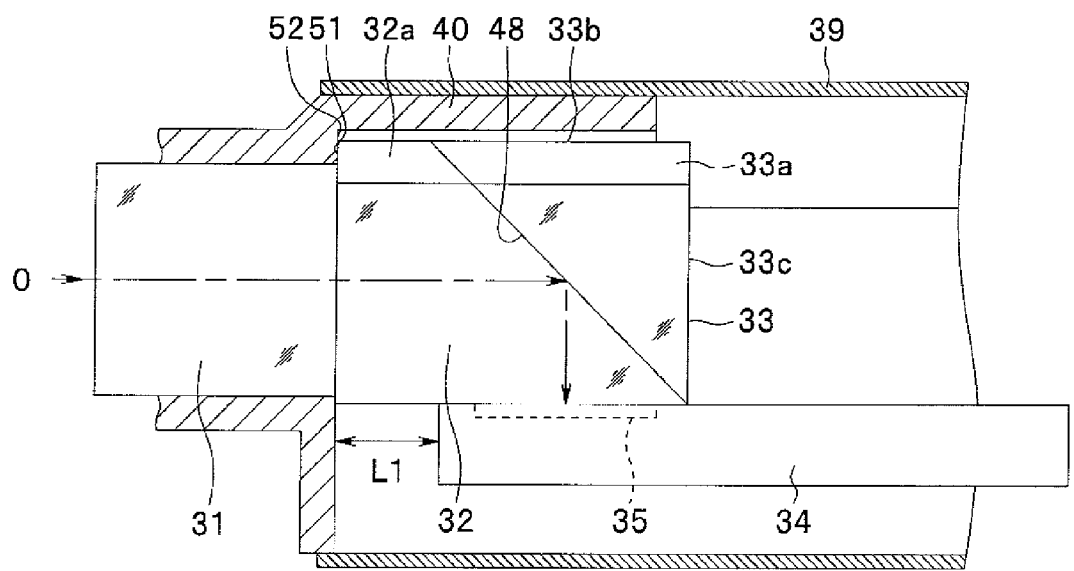
FIG. 8 is a right side view showing in cross section a part of the image pickup unit fixed to the lens frame and the reinforcing frame according to the first embodiment of the present invention.

FIG. 1 to FIG. 8 relate to the first embodiment. FIG. 1 is a view showing a configuration of an electronic endoscope system. FIG. 2 is a sectional view of a distal end portion of the electronic endoscope. FIG. 3 is a sectional view of the distal end portion of the electronic endoscope along the line III-III in FIG. 2. FIG. 4 is an exploded perspective view of the image pickup unit. FIG. 5 is a rear right side perspective view of a part of the image pickup unit after being assembled from the state shown in FIG. 4. FIG. 6 is a front view of the image pickup unit. FIG. 7 is a top view showing in cross section a part of the image pickup unit fixed in a unit holding frame and a reinforcing frame. FIG. 8 is a right side view showing in cross section a part of the image pickup unit fixed to the unit holding frame and the reinforcing frame.

As shown in FIG. 1, an electronic endoscope system 1 is configured by an electronic endoscope (hereinafter simply referred to as endoscope) 2, a light source apparatus 3, a video processor 4 and a monitor 5.

The endoscope 2 according to the present embodiment includes an elongated insertion portion 6 and an operation portion 7 continuously connected to the proximal end of the insertion portion 6. The insertion portion 6 of the endoscope 2 includes a distal end portion 8 which is provided at the distal end of the insertion portion 6, a bending portion 9 which is provided on the proximal end side of the distal end portion 8, and which is configured by a plurality of bending pieces so as to be freely bendable, and a flexible tube portion 10 which is elongated and flexible and is provided on the proximal end side of the bending portion 9.

An image pickup apparatus as will be described below is incorporated in the distal end portion 8. The image pickup apparatus includes an image pickup device, such as a CCD and a CMOS, which photoelectrically converts an optical image formed by an objective optical system provided in the distal end portion 8.

In the endoscope 2, a universal cord 15, in which illumination light transmission means such as a light guide bundle as will be described below, and the like, is inserted, is extended from a side portion of the operation portion 7. The universal cord 15 is detachably connected to the light source apparatus 3 via a light guide connector 16 provided at the end of the universal cord 15.

The endoscope 2 is detachably connected to the video processor 4 via an electric connector 18 provided at the end of a scope cable 17 which is a signal cable extended from a side portion of the light guide connector 16. Note that the video processor 4 is freely connected to peripheral apparatuses, such as a VTR deck, a video printer, and a videodisk (all not shown).

Here, two substantially disk-like bending operation knobs 11 are provided in the operation portion 7. The bending operation knobs 11 are configured such that the bending portion 9 is bent in four directions or in two directions in accordance with the rotating operation of the knobs. Further, a plurality of switches 12 and 13 are provided in the operation portion 7. The switches 12 and 13 are operated when a predetermined endoscope function is to be performed.

Further, a treatment instrument insertion port 14, through which a treatment instrument such as a biopsy forceps and a laser probe is inserted, is provided in a side portion in the vicinity of the distal end of the operation portion 7. With the endoscope 2 in the state where the treatment instrument is inserted through the treatment instrument insertion port 14, and where a distal end treatment portion of the treatment instrument is made to project through a treatment instrument insertion channel provided in the endoscope 2, it is possible to perform a treatment, such as a biopsy for collecting an affected tissue by the use of, for example, the biopsy forceps which is one of the treatment instruments.

The light source apparatus 3 according to the present embodiment is an apparatus in which a halogen lamp, or the like, is incorporated, and which supplies the light from the halogen lamp, as illumination light, to the endoscope 2 connected to the light source apparatus 3.

Further, the video processor 4 is an apparatus which supplies power to the image pickup apparatus provided in the distal end portion 8, and into which a photoelectrically converted video signal from the image pickup device of the image pickup apparatus is inputted. That is, the video processor 4 performs processing of the video signal picked up by the image pickup device, control processing such as the gain adjustment of the image pickup device, and output of a drive signal for driving the image pickup device.

The monitor 5 is used to receive the video signal outputted from the video processor 4 connected to the monitor 5, so as to display an endoscopic image. The monitor 5 in the present embodiment is configured such that an octagonal endoscopic image whose four corners are cut by being electronically masked is displayed in the monitor screen 5a.

Next, there will be described in detail a configuration of the distal end portion 8 of the endoscope 2 according to the present embodiment with reference to FIG. 2 to FIG. 8.

First, as shown in FIG. 2, the distal end portion 8 of the endoscope 2 is covered by a distal end cover 22 formed of synthetic resin or the like, and is provided with a distal end frame 21 which configures a substantially columnar metallic distal end portion main body in which a plurality of holes are formed inside.

A channel line 23 which configures a distal end portion of a treatment instrument insertion channel 24, a light guide bundle 27 for transmitting the illumination light from the light source apparatus 3 (see FIG. 1), and an image pickup unit 30 are fitted into the inside of the distal end frame 21.

The channel line 23 is configured to have an opening (not shown) in the distal end surface of the distal end portion 8 and to make the treatment instrument insertion channel 24 communicate with the treatment instrument insertion port 14 (see FIG. 1) of the operation portion 7.

The light guide bundle 27 is arranged in a metallic light guide holding tube 26 in the distal end portion 8, and is also arranged in a flexible tube 25 in the range from around the light guide holding tube 26 to the light guide connector 16 (see FIG. 1).

Note that the channel line 23 and the light guide holding tube 26 are fixed to the distal end frame 21 with screws (not shown).

Next, there will be described the image pickup unit 30 arranged in the distal end portion 8.

As shown in FIG. 3, the image pickup unit 30 is mainly configured by an objective lens group 41, a lens holding frame 42 for holding the objective lens group 41, a unit holding frame 40 externally fitted and fixed to the lens holding frame 42, a cover glass 31, a prism 32 which is an optical reflection member whose front surface is joined with the rear surface of the cover glass 31, a protection member 33 joined with the reflection surface of the prism 32, a solid-state image pickup device 34 joined, in FIG. 3, with the lower surface of the prism 32, and a substrate 36 on which an electronic component 37 and the like is mounted and is electrically connected to the solid-state image pickup device 34.

The lens holding frame 42 is fitted and fixed to the distal end frame 21, and the unit holding frame 40 is externally inserted and fixed to the proximal end outer peripheral portion of the lens holding frame 42. The cover glass 31 is inserted into the inside of the proximal end side of the unit holding frame 40. The unit holding frame 40 substantially includes therein the prism 32, the protection member 33, and the solid-state image pickup device 34.

The distal end portion of a reinforcing frame member 39 covering the periphery of the prism 32, the protection member 33, and the solid-state image pickup device 34, which are included in the unit holding frame 40, is externally fitted and fixed to the proximal end portion outer circumference of the unit holding frame 40. The reinforcing frame member 39 is a metallic cylindrical member having an octagonal cross section (see FIG. 2).

Note that the solid-state image pickup device 34 according to the present embodiment, which uses an image sensor, such as a CMOS or a CCD, for photoelectrically converting photographing light, has a light receiving portion 35 for receiving the photographing light reflected by the prism 32. In FIG. 3, the light receiving portion 35 is positioned on the upper surface of the solid-state image pickup device 34, which surface is set to face the lower surface of the prism 32.

Further, the solid-state image pickup device 34 is electrically connected to one end of an image-pickup signal communication cable 38 which is inserted and arranged to reach the light guide connector 16 of the universal cord 15 shown in FIG. 1. That is, an image-pickup signal formed by photoelectrically converting the photographing light made incident on the light receiving portion 35 of the solid-state image pickup device 34, is transmitted to the light guide connector 16 via the image-pickup signal communication cable 38, and is outputted to the video processor 4 via the electric connector 18 of the scope cable 17. The image-pickup signal is subjected to video processing by the video processor 4, and is displayed as an endoscopic image in the monitor screen 5a of the monitor 5.

Here, with reference to FIG. 4 and FIG. 5, there will be described in detail a configuration of each of the cover glass 31, the prism 32, and the protection member 33, and a configuration assembled in such a way that the cover glass 31, the prism 32, and the protection member 33 are joined with each other and thereafter joined at a predetermined position of the solid-state image pickup device 34.

As shown in FIG. 4, the cover glass 31 has a substantially columnar shape, and the rear surface of the cover glass 31 is bonded to the front surface of the prism 32.

The prism 32 has an inclined rear surface serving as a reflection surface 48 which refracts the photographing light introduced into the prism 32 to the lower side, and has tapered surfaces 32a which are chamfers formed by cutting both side corner portions on the upper side of the prism 32.

In the present embodiment, the protection member 33 is formed of the same material as that of the prism 32 or formed of a light transmissive transparent glass member having the same linear expansion coefficient (thermal expansion coefficient) as that of the prism 32. The front surface of the protection member 33 is formed to have an inclined surface, which is inclined at the same angle as the reflection surface 48 of the prism 32 so as to be surface-joined with the reflection surface 48, and the protection member 33 has tapered surfaces 33a which are respectively formed to lie in the same surfaces as the tapered surfaces 32a of the prism 32 in such a way that chambers are formed by cutting (one side corner portion or) both side corner portions on the upper side of the protection member 33.

The tapered surfaces 32a and 33a are configured so as to correspond to the shapes of the unit holding frame 40 and of the reinforcing frame member 39 which cover the tapered surfaces 32a and 33a at a predetermined distance away from the periphery of the tapered surfaces 32a and 33a. Also, the tapered surfaces 32a and 33a are configured in such a way that one or two corner portions of the upper side of the prism 32 and of the protection member 33, which portions are optically unnecessary to the photographing light, are cut in order to reduce a space for mounting the image pickup unit 30 in the distal end frame 21 of the distal end portion 8, and to thereby efficiently arrange the other components in a limited space.

Note that the protection member 33 is configured such that the respectively corresponding surfaces and end portion (the upper surface, the lower end portion, the side surfaces, and the tapered surfaces 33a) of the protection member 33 are respectively set to lie in the same surfaces as (that is, are respectively formed as continuous surfaces without a level difference from) all the surfaces of the upper surface, the lower surface, the side surfaces and the tapered surfaces 32a of the prism 32, that is, each surface being a continuous surface without any unevenness. That is, the prism 32 and the protection member 33 configure one block body in which all the peripheral shapes of the upper, lower and side portions joined by the reflection surface 48 are the same.

Note that the protection member 33 has a joining surface which is an inclined surface joined with the reflection surface 48 of the prism 32 and which is formed to reach a rear surface portion 33c, and hence has no lower surface. Thus, a portion arranged so as to lie in the same surface as the lower surface of the prism 32 becomes the lower end portion formed by the joining surface and the rear surface portion 33c.

Further, in the protection member 33 according to the present embodiment, as shown in FIG. 4 and FIG. 5, an upper surface portion 33b is set to lie in the same surface as the upper surface of the joined prism 32, and the rear surface portion 33c is set to be in parallel with the front surface of the prism 32.

In other words, the protection member 33 has the upper surface portion 33b which is substantially in parallel with the lower surface of the prism 32, and which is in parallel with the light receiving surface of the solid-state image pickup device 34, on which light receiving surface the light receiving portion 35 joined to the lower surface of the prism 32 is arranged. Further, the protection member 33 has the proximal end side rear surface portion 33c which is perpendicular to the optical axis O of the photographing light made incident on the prism 32 from the photographing object point via the cover glass 31 joined with the front surface of the prism 32.

Further, the rear surface of the cover glass 31 is joined with the front surface of the prism 32, and the reflection surface 48 of the prism 32 is joined with the front surface of the protection member 33 by, for example, an ultraviolet curing adhesive or an ultraviolet and thermosetting curing adhesive (hereinafter simply referred to as UV adhesive) which have a short curing time.

That is, in the present embodiment, the protection member 33 is formed of a transparent glass member. Thus, the opaque reflection surface 48 of the prism 32 can be joined with the protection member 33 in such a way that the ultraviolet ray is made to pass through the transparent protection member 33 to be irradiated to the UV adhesive which is applied to the joining surface between the reflection surface 48 and the protection member 33. Note that after being joined with each other by the UV adhesive, the prism 32 and the protection member 33 may be subjected to the cutting machining so as to be formed into a predetermined shape as a whole.

Further, the protection member 33 according to the present embodiment is integrally joined with the prism 32 and has the rear surface portion 33c in parallel with the front surface of the prism 32. Thus, the protection member 33 according to the present embodiment has an advantage that the side of the prism 32 can be easily grasped at the time of optical alignment, and thereby the assembling property in joining the rear surface of the cover glass 31 with the front surface of the prism 32 is significantly improved.

Note that the protection member 33 is preferably formed of a material having the same linear expansion coefficient (thermal expansion coefficient) as that of the material of the prism 32, but the material of the protection member 33 is not limited thereto. For example, an opaque material, such as a synthetic resin or metal, which has a linear expansion coefficient (thermal expansion coefficient) approximately equal to that of the material of the prism 32, may also be used as the material of the protection member 33. In this case, a UV adhesive to which the ultraviolet ray needs to be irradiated for joining the prism 32 with the protection member 33, cannot be used, and hence a thermosetting adhesive is used.

Further, the prism 32 is optically aligned so that the photographing light refracted by the reflection surface 48 is received at a predetermined position of the light receiving portion 35 of the solid-state image pickup device 34, and is then positioned so as to be bonded and fixed. That is, as shown in FIG. 5, the lower surface of the prism 32 is joined on the solid-state image pickup device 34 by, for example, a UV adhesive.

At this time, in the present embodiment, there is an advantage that the assembling property is significantly improved because the protection member 33 integrally joined with the prism 32 has the upper surface portion 33b which is in parallel with the lower surface of the prism 32, and hence because, in the case where the lower surface of the prism 32 is joined with the surface on which the light receiving portion 35 of the solid-state image pickup device is arranged, the side of the prism 32 can be easily grasped at the time of optical alignment, to thereby be easily pressed down.

Further, on the reflection surface 48 of the prism 32, there is formed a mirror film which is a thin film attached to the surface of the reflection surface 48 by vapor deposition, or the like. The photographing light refracted and reflected by the reflection surface 48 is received by the light receiving portion 35 of the solid-state image pickup device 34. Further, on the reflection surface 48, there is set an effective reflection surface 45, as shown in FIG. 6, which is an octagonal area to make the reflection effectively performed in correspondence with the octagonal photographing range in which the photographing light received by the solid-state image pickup device 34 is displayed in the monitor screen 5a of the monitor 5 as shown in FIG. 1 after being photoelectrically converted and electronically masked.

Further, in the present embodiment, in the state where the prism 32 is joined with the solid-state image pickup device 34, as shown in FIG. 5, the front end surface of the solid-state image pickup device 34 is positioned behind the front surface of the prism 32 by a predetermined length 11.

Among the cover glass 31, the prism 32, the protection member 33, and the solid-state image pickup device 34 which are joined and assembled to each other as described above, the cover glass 31 is first inserted and fitted from the rear side so as to be included in the unit holding frame 40 as shown in FIG. 7 and FIG. 8. Further, although not shown in FIG. 7 and FIG. 8, the solid-state image pickup device 34 is electrically connected to the substrate 36 to which the electronic component 37 shown in FIG. 3 is mounted and to which element wires of the image-pickup signal communication cable 38 are joined with solder, or the like.

When the cover glass 31, the prism 32, the protection member 33, and the solid-state image pickup device 34, which are assembled as described above, are fixed to the unit holding frame 40, a front prism side joining surface 51 to which the cover glass 31 of the prism 32 is not joined is positioned by being brought into contact with a holding frame side joining surface 52 of a step formed in the proximal end portion of the unit holding frame 40, to which portion the cover glass 31 is inserted and fitted as shown in FIG. 7 and FIG. 8.

In the present embodiment, the prism side joining surface 51 is fixed to the holding frame side joining surface 52 by, for example, the UV adhesive, and the cover glass 31, the prism 32, the protection member 33, and the solid-state image pickup device 34 which are assembled in this way are fixed to the unit holding frame 40.

Further, the present embodiment is configured such that the front end surface of the solid-state image pickup device 34 is positioned behind the front surface of the prism 32 by the predetermined distance 11, and hence the solid-state image pickup device 34 is prevented from being brought into contact with the unit holding frame 40. Thereby, the solid-state image pickup device 34 is electrically insulated from the metallic unit holding frame 40, and is assembled in a state where the electric short circuit is prevented.

Note that in the inside of the unit holding frame 40 and the reinforcing frame member 39, a thermosetting filler may be provided around the prism 32, the protection member 33, and the solid-state image pickup device 34.

As described above, in the configuration of the distal end portion 8 of the electronic endoscope 2 according to the present embodiment, the protection member 33 is surface-joined with the whole reflection surface 48 so as to prevent the reflection surface 48 of the prism 32 from being exposed. Thereby, at the time of assembling, maintenance, and the like, of the image pickup unit 30, the reflection surface 48 is covered by the protection member, so as to be prevented from being brought into direct contact with the other components. Thus, it is possible to prevent the reflection surface 48 of the prism 32 from being damaged or chipped.

Further, the protection member 33 according to the present embodiment is formed of the same material, such as the glass material, as that of the prism 32. Thereby, in a medical apparatus, such as the endoscope 2, which before and after being used, is subjected to the autoclave treatment by a high temperature and high pressure sterilization apparatus, it is possible to prevent the separation in the adhesive-joining portion between the protection member 33 and the prism 32. That is, the protection member 33 is formed of a material having the same or approximately the same linear expansion coefficient (thermal expansion coefficient) as that of the prism 32, and thereby the degree of expansion and contraction of the protection member 33, which is caused by a change from a normal temperature to a high temperature and by a change from the high temperature to the normal temperature, is made to become substantially the same as that of the prism 32. Thereby, the adhesive bonded joining surface between the prism 32 and the protection member 33 is hardly separated, so that the reflection surface 48 of the prism 32 is prevented from being damaged. Further, the prism 32 and the protection member 33 are formed of a material having the same or approximately the same thermal expansion coefficient (linear expansion coefficient) as that of the solid-state image pickup device 34, and thereby the degree of expansion and contraction of the prism 32 and the protection member 33, which is caused by a change from a normal temperature to a high temperature and by a change from the high temperature to the normal temperature, is made to become substantially the same as that of the solid-state image pickup device 34. Thereby, the adhesive bonded joining surface between the prism 32 and the solid-state image pickup device 34 is hardly separated, and the image pickup unit 30 is prevented from being damaged.

Further, the protection member 33 according to the present embodiment is formed of the transparent material. Thereby, the protection member 33 and the reflection surface 48 of the prism 32, when being surface-joined, can be fixed to each other by using the UV adhesive. This makes it possible to reduce the curing time at the time of joining after the mutual alignment positions are specified, as compared with the case where a thermosetting adhesive or the like is used, and also makes it possible to reduce the time during which the protection member 33 and the prism 32 are respectively held. As a result, the prism 32 and the protection member 33 can be fixed in a short time, so as to provide a configuration in which the predetermined optical performance can be easily maintained at the time of assembling.

Further, the prism 32 and the protection member 33 which are joined to each other, are configured as one block body in such a state where all the peripheral shapes of the upper and lower portions and of the both side portions of the protection member 33, which are joined by the reflection surface 48, are the same as the peripheral shapes of the prism 32. In particular, the protection member 33 has the upper surface portion 33b which is in parallel with the lower surface of the prism 32, and the rear surface portion 33c which is in parallel with the front surface of the prism 32. Therefore, the protection member 33 is configured into a shape which can be easily grasped, and configured so as to be easily pressed onto the other components to be joined.

Further, the prism 32 and the protection member 33 are configured such that the tapered surfaces 32a and 33a are formed in the corner portions between the upper surface and the both side surfaces. Thereby, the image pickup unit 30 and other built-in components can be efficiently arranged in the limited space in the distal end portion 8 which is desired to be made thin.

Note that in the present embodiment, the solid-state image pickup device 34 is joined with the prism 32 at the position where the end surface on the distal end side of the joined solid-state image pickup device 34 is separated from the front surface of the prism 32 by the length 11 and thereby the solid-state image pickup device 34 is prevented from being interfered with the unit holding frame 40. For this reason, the solid-state image pickup device 34 is assembled in the state where the insulation between the solid-state image pickup device 34 and the other metal components (unit holding frame 40) is maintained.

(Second Embodiment)

Next, there will be described a second embodiment of the image pickup unit according to the present invention. The second embodiment will be described in detail below with reference to FIG. 9 to FIG. 16. Note that in the following description, the same components as those in the first embodiment are denoted by the same reference numerals and characters, and the detailed description thereof is omitted.

Figure 9:
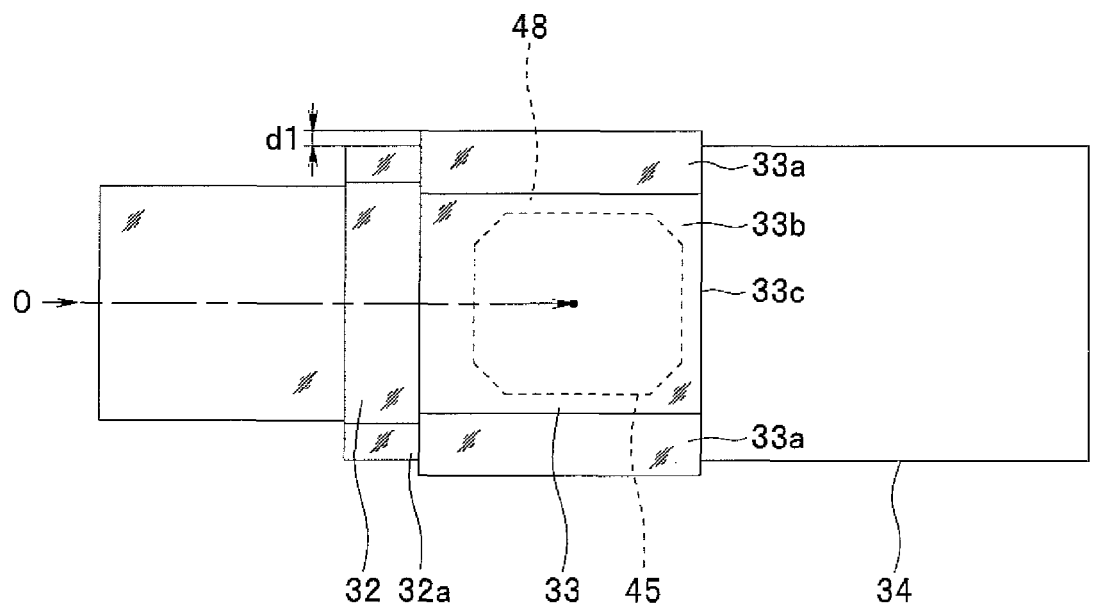
FIG. 9 is a top view showing a part of an image pickup unit according to a second embodiment of the present invention.
Figure 10:
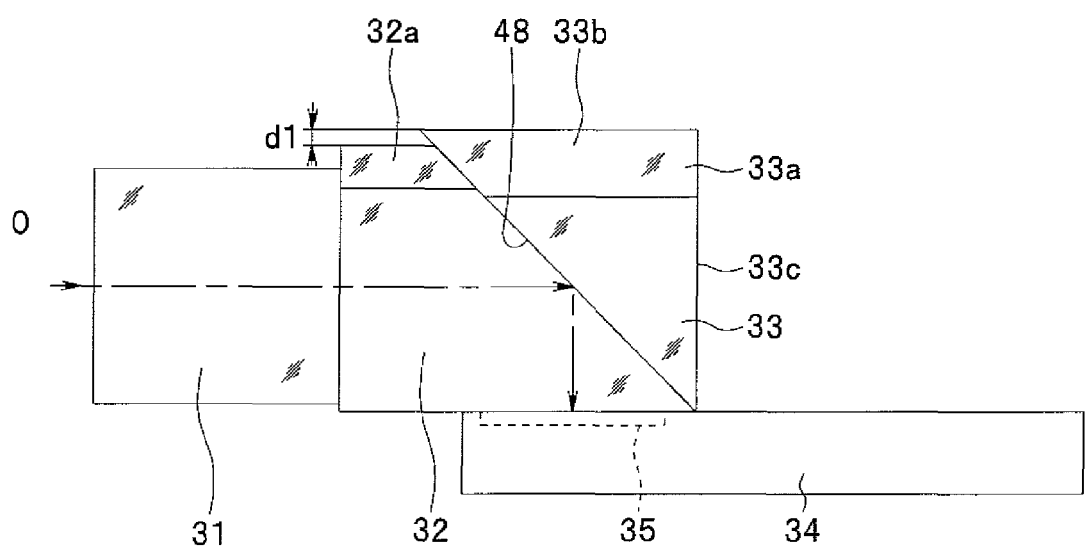
FIG. 10 is a right side view showing a part of the image pickup unit according to the second embodiment of the present invention.
Figure 11:
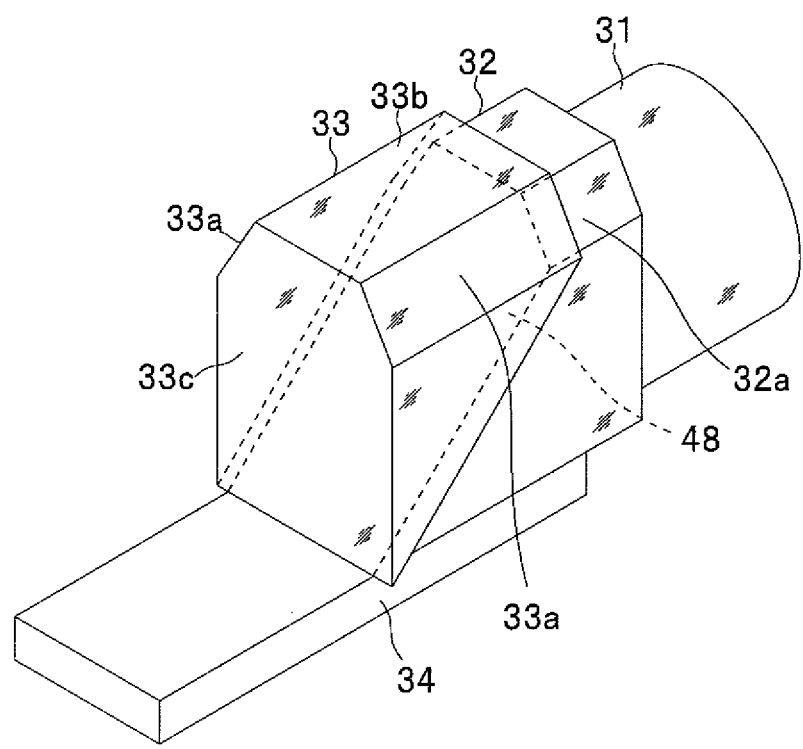
FIG. 11 is a rear right side perspective view showing a part of the image pickup unit after being assembled according to the second embodiment of the present invention.
Figure 12:
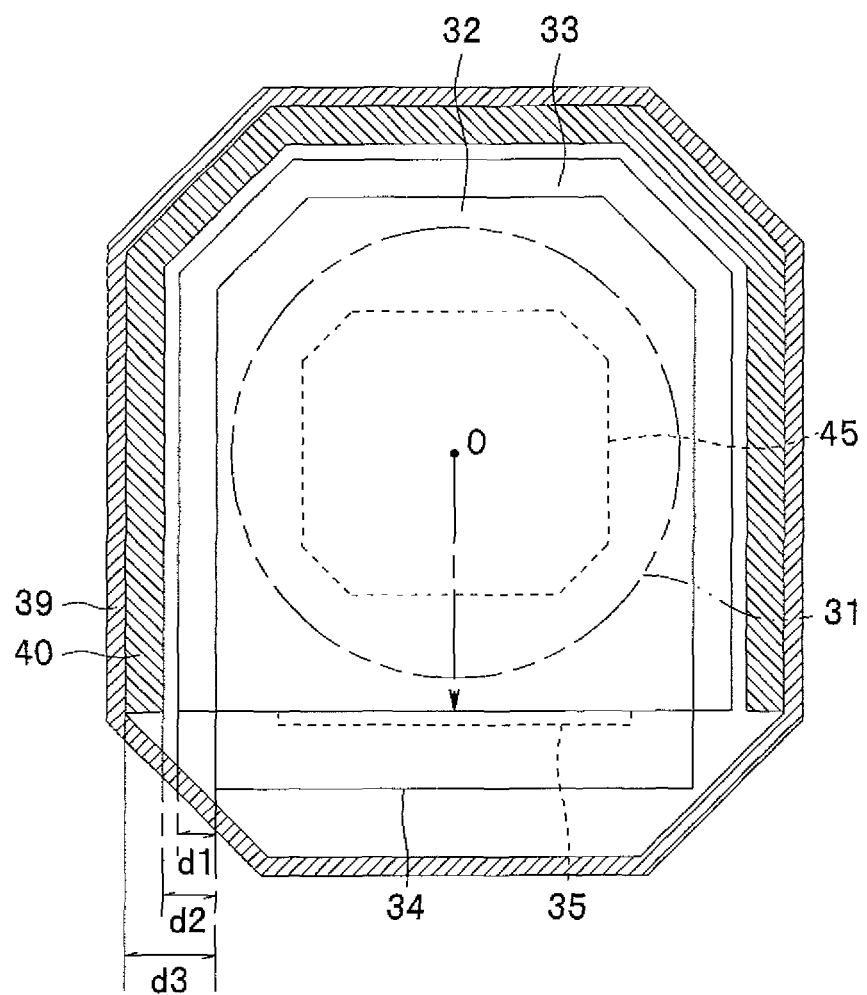
FIG. 12 is a front view showing in cross section a part of the image pickup unit fixed to the lens frame and the reinforcing frame according to the second embodiment of the present invention.
Figure 13:
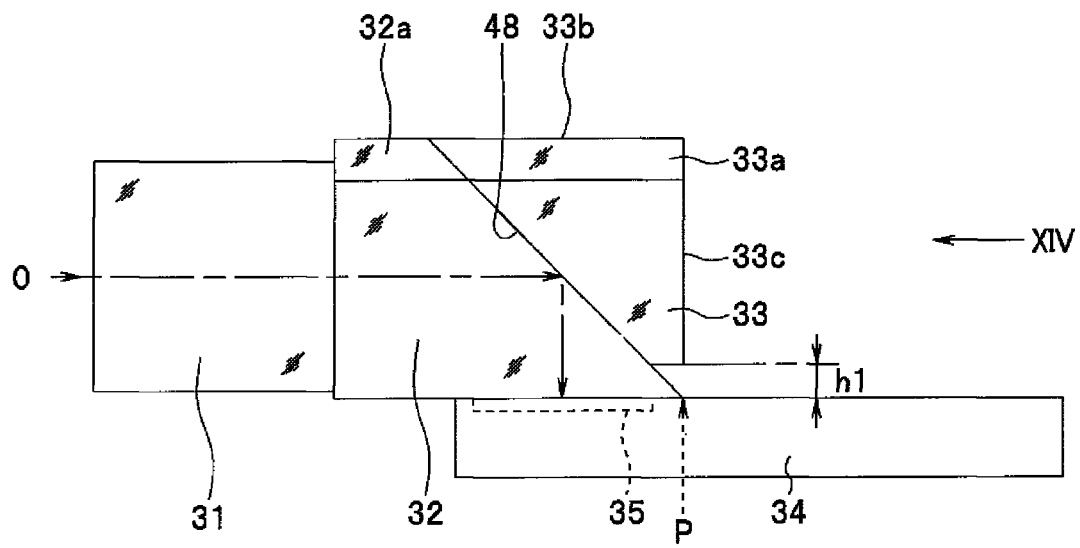
FIG. 13 is a right side view showing a part of an image pickup unit according to a first modification of the second embodiment of the present invention.
Figure 14:
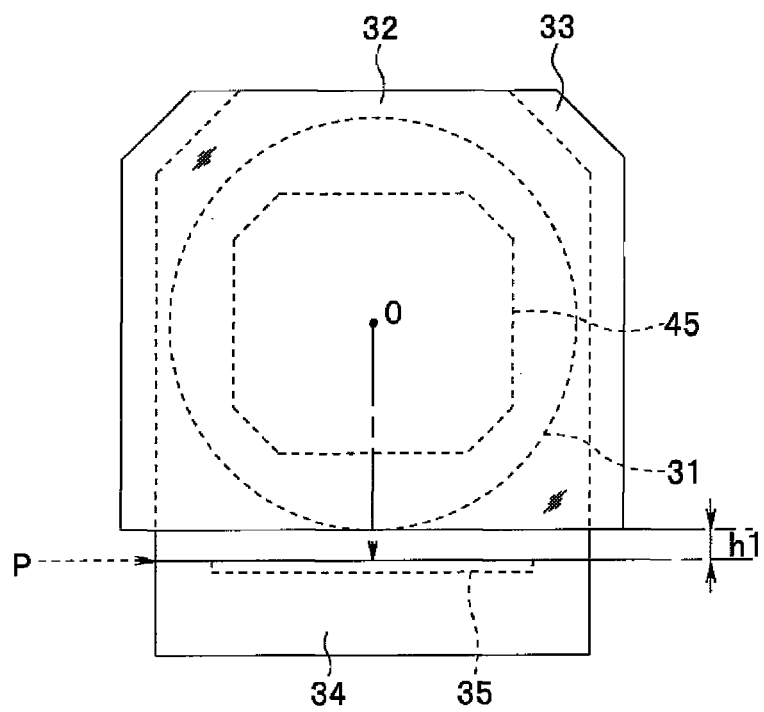
FIG. 14 is a rear view showing the rear side of the image pickup unit corresponding to the view XIV in FIG. 13 according to the first modification of the second embodiment of the present invention.
Figure 15:
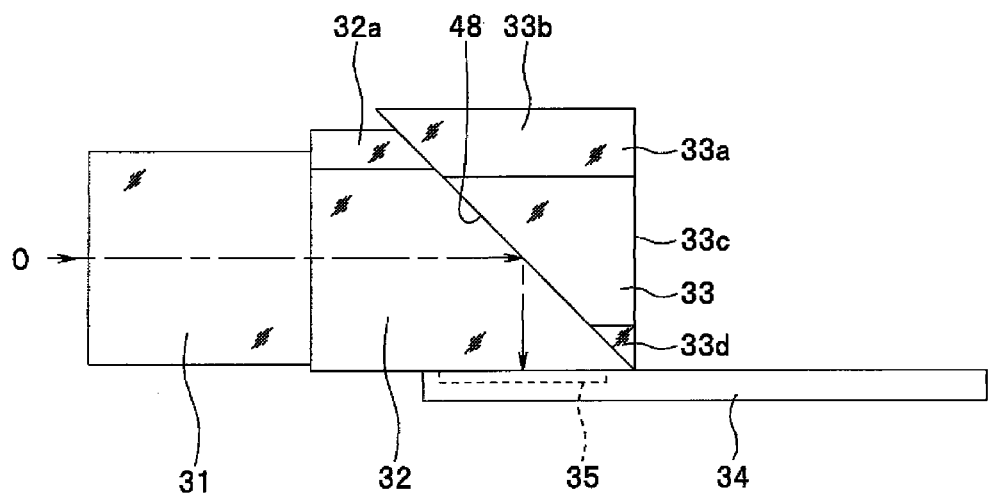
FIG. 15 is a right side view showing a part of an image pickup unit according to a second modification of the second embodiment of the present invention.
Figure 16:
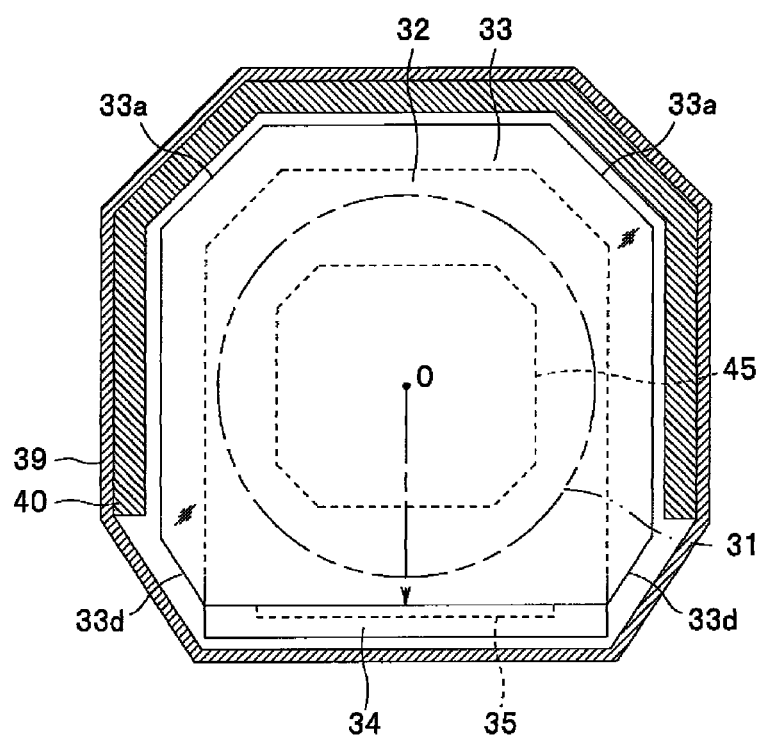
FIG. 16 is a front view showing in cross section a part of the image pickup unit of FIG. 15 fixed to the lens frame and the reinforcing frame according to the second modification of the second embodiment of the present invention.

Further, FIG. 9 to FIG. 16 relate to the second embodiment according to the present invention. FIG. 9 is a top view showing a part of an image pickup unit. FIG. 10 is a right side view showing a part of the image pickup unit. FIG. 11 is a rear right side perspective view showing a part of the image pickup unit after assembling. FIG. 12 is a front view showing in cross section a part of the image pickup unit fixed to the lens frame and the reinforcing frame. FIG. 13 is a right side view showing a part of an image pickup unit of a first modification. FIG. 14 is a rear view showing the rear side of the image pickup unit corresponding to the view XIV in FIG. 13. FIG. 15 is a right side view showing a part of the image pickup unit of the second modification. FIG. 16 is a front view showing in cross section a part of the image pickup unit which is fixed in the lens frame and the reinforcing frame shown in FIG. 15.

The configuration of the present embodiment is different from that of the first embodiment only in the shape of the protection member 33 joined to the prism 32.

As shown in FIG. 9 to FIG. 11, in the protection member 33 according to the present embodiment, each of the surfaces (the upper surface, the side surfaces, and the tapered surfaces 33a), which respectively correspond to the surfaces of the upper surface, the side surfaces, and the tapered surfaces 32a of the side portions of the prism 32, except the lower surface joined with the solid-state image pickup device 34, is set to be extended to the outer side by a distance d1. In other words, the external shape of the protection member 33 is configured such that the upper surface, the side surfaces, and the tapered surfaces 33a are set to the outside by the distance d1 from the upper surface, the side surfaces, and the tapered surfaces 32a of the prism 32, in the state where the surface positions are aligned so as to make the lower surface of the protection member 33 lie in the same surface as the lower surface of the prism 32.

Then, similarly to the first embodiment, the cover glass 31, the prism 32, the protection member 33, and the solid-state image pickup device 34, which are integrally assembled as shown in FIG. 11, are joined in the unit holding frame 40, and is covered by the reinforcing frame member 39, as shown in FIG. 12.

In this state, the outer periphery of the protection member 33 except the lower surface is set larger than that of the prism 32 by the length d1 so as to prevent the prism 32 from being interfered with, that is, being brought into contact with the inner surface of the unit holding frame 40, which surface faces the prism 32. For example, when the distance (length) of the gap between the external surface of the prism 32 and the inner surface of the unit holding frame 40, which surfaces face each other, is set to d2 as shown in FIG. 12, the above described length d1 of the protection member 33 is set shorter than the distance (length) d2 (d1<d2).

Note that it is needless to say that the above described length d1 of the protection member 33 is set so as to also prevent the protection member 33 from being interfered with (being brought into contact with) the reinforcing frame member 39 externally fitted to the unit holding frame 40. That is, for example, as shown in FIG. 12, when the distance (length) of a gap between the external surface of the prism 32 and the inner surface of the reinforcing frame member 39, which face each other, is set to d3, it is obvious that the length d1 of the protection member 33 is set shorter than the distance (length) d3 (d1<d3).

That is, the protection member 33 has external surfaces (the upper surface, the side surfaces, and the tapered surfaces 33a) which are set to be larger than the upper surface, the side surfaces, and the tapered surfaces 32a of the prism 32, within the range of the gap between the exposed external surface of the prism 32 and the inner surface of the unit holding frame

40. Further, similarly to the first embodiment, the whole reflection surface 48 of the prism 32 is surface-joined to the protection member 33.

In the present embodiment as described above, in addition to the effect of the first embodiment, there is an advantage that the prism 32 itself is further prevented from being damaged, because at the time of the assembling, maintenance, and the like, of the image pickup unit 30, even when the component formed by integrating the prism 32 and the protection member 33 is brought into contact with the other components, or the like, the external portion of the protection member 33 is mostly brought into contact with the other components, or the like, prior to the prism 32.

It is particularly important to protect the reflection surface 48 for refraction and reflection of the prism 32, and hence the protection member 33 which is surface-joined to the periphery of the reflection surface 48 is configured to project to the external side. That is, in the configuration of the distal end portion 8 of the electronic endoscope 2 according to the present embodiment, the protection member 33 prevents, at the time of the assembling, maintenance, and the like, the portion in the vicinity of the reflection surface 48 of the prism 32 from being brought into contact with the other components, and hence the reflection surface 48 can be sufficiently protected.

Note that, as shown in FIG. 13 and FIG. 14, a lower end portion is formed by cutting a portion ranging from the joining surface of the protection member 33, which surface is joined to the reflection surface 48 of the prism 32, to the rear surface portion 33c of the protection member 33 so that a gap between the lower end portion and the upper surface of solid-state image pickup device 34, which surface is joined to the prism 32, is formed to have a predetermined length h1.

The lower end portion of the protection member 33 is cut to provide the gap having the predetermined length h1 between the lower end portion and the solid-state image pickup device 34. Thereby, when the prism 32 integrally joined with the protection member 33 is joined with the solid-state image pickup device 34, the protection member 33 is prevented form being brought into contact with the solid-state image pickup device 34. That is, a mechanical stress is prevented from being applied by the protection member 33 to the solid-state image pickup device 34. Thus, it is possible to surely join the prism 32 to the solid-state image pickup device 34, and also possible to prevent the separation of the respective bonded surfaces between the prism 32 and the protection member 33, and between the prism 32 and the solid-state image pickup device 34.

Further, it is possible to easily specify the optical alignment position P where the prism 32 is joined to the surface on which the receiving portion 35 of the solid-state image pickup device 34 is provided. That is, it is possible to easily measure the distance from the light receiving portion 35 of the solid-state image pickup device 34, to thereby align the rear end portion of the lower surface of the prism 32 to the position P on the solid-state image pickup device 34, which position specifies predetermined optical performance.

Further, as shown in FIG. 15 and FIG. 16, there may be formed tapered surfaces 33d which are chamfered portions formed by cutting both the lower corner portions of the protection member 33, which corner portions are projected from the prism 32 to the outer direction.

In this way, the tapered surfaces 33b and 33d are formed by chamfering the four corners of the protection member 33. Thereby, as shown in FIG. 16, in the present embodiment, it is possible to reduce the size of the reinforcing frame member 39 in correspondence with the external shape of the protection member 33, and possible to further reduce the size of the external shape of the image pickup unit 30.

(Third Embodiment)

Next, a third embodiment of the image pickup unit according to the present invention will be described in detail below with reference to FIG. 17 to FIG. 20. Note that also in the following description, the same components as those in the above described first embodiment are denoted by the same reference numerals and characters, and the explanation thereof is omitted.

Figure 17:
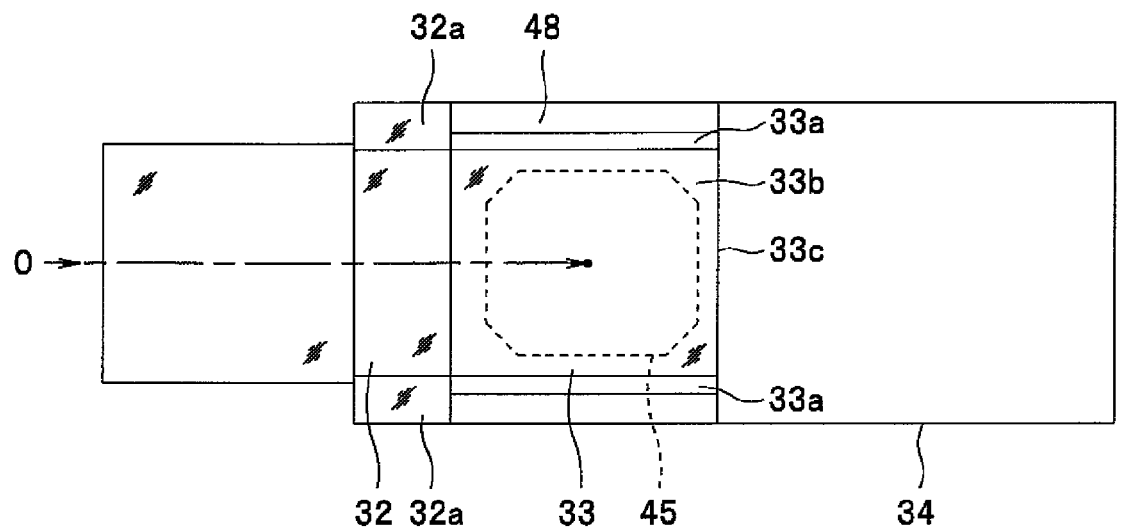
FIG. 17 is a top view showing a part of the image pickup unit according to a third embodiment of the present invention.
Figure 18:
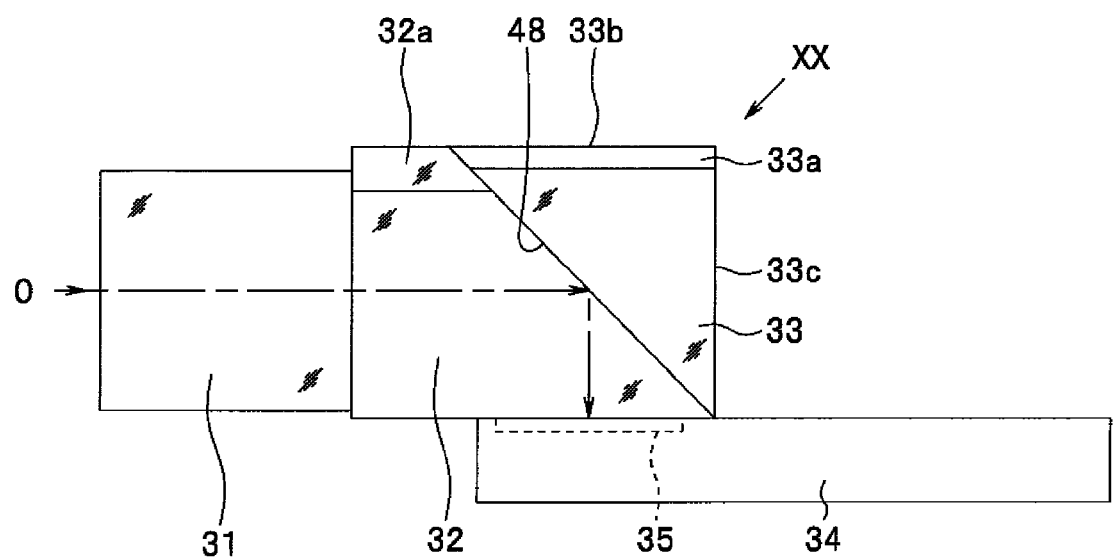
FIG. 18 is a right side view showing a part of the image pickup unit according to the third embodiment of the present invention.
Figure 19:
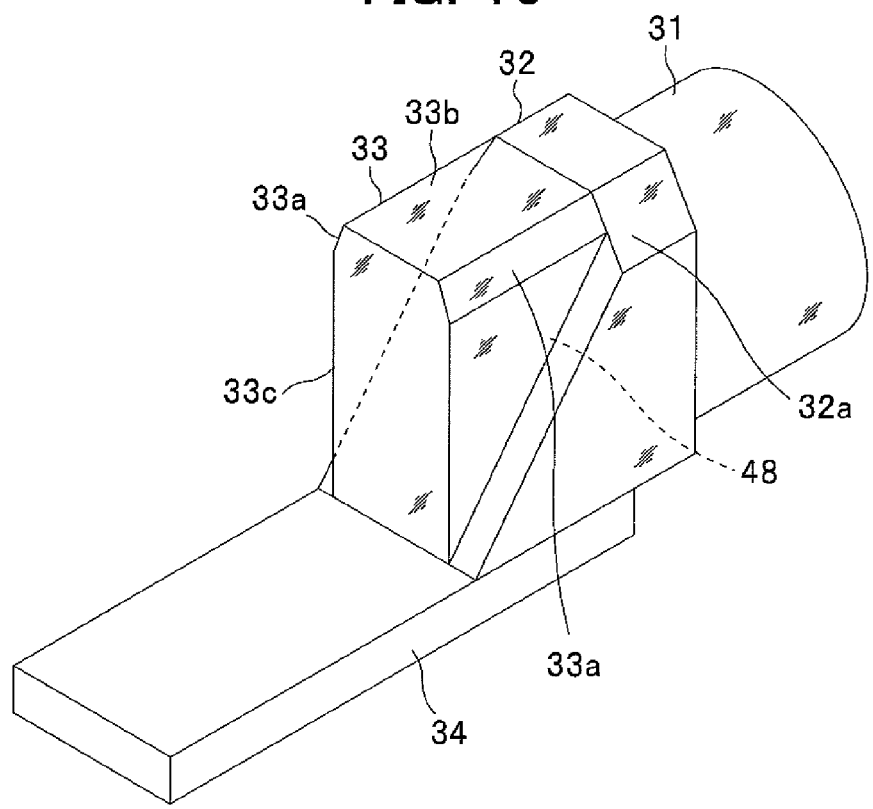
FIG. 19 is a rear right side perspective view showing a part of the image pickup unit after being assembled according to the third embodiment of the present invention.
Figure 20:
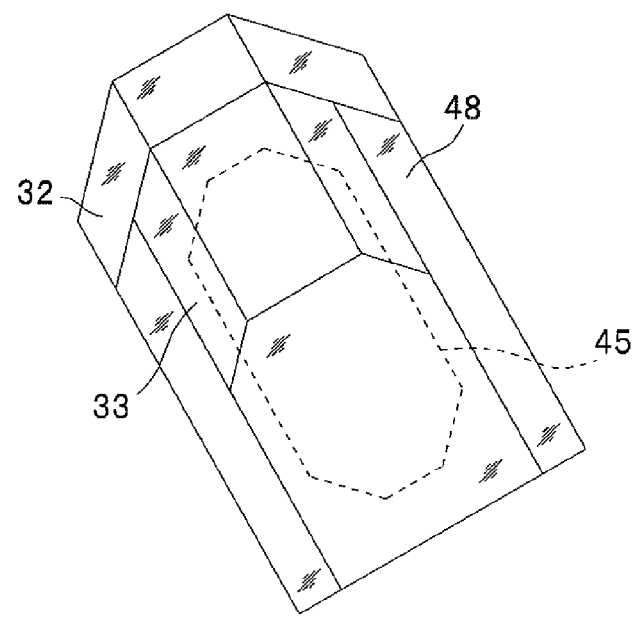
FIG. 20 is a plan view showing a prism and a protection member corresponding to the view XX in FIG. 18 according to the third embodiment of the present invention.

FIG. 17 to FIG. 20 relate to the third embodiment according to the present invention. FIG. 17 is a top view showing a part of an image pickup unit. FIG. 18 is a right side view showing a part of the image pickup unit. FIG. 19 is a rear right side perspective view showing a part of the image pickup unit after assembling. FIG. 20 is a plan view corresponding to the view XX in FIG. 18.

In the present embodiment, the protection member 33 joined to the prism 32 is configured to have a shape which is different from the shape of the first embodiment in that the area of the joining surface with the prism 32 is smaller than the area of the reflection surface 48, and larger than the area of the effective reflection surface 45 within the reflection surface 48.

Specifically, as shown in FIG. 17 to FIG. 19, the joining surface of the protection member 33 having an area, which is larger than the area of the effective reflection surface 45 within the reflection surface 48 of the prism 32 and is smaller than the reflection surface 48, is joined so as to cover the effective reflection surface 45 of the prism 32.

Further, in the present embodiment, the upper surface and the lower surface of the protection member 33 are respectively positionally aligned to the upper surface and the lower surface of the prism 32, and the width between the both side surfaces of the protection member 33 is set smaller than the width of the prism 32, that is, the width of the reflection surface 48. That is, as shown in FIG. 20, the protection member 33 is joined to the reflection surface 48 so as to cover at least the range of the effective reflection surface 45 of the prism 32.

That is, the protection member 33 is configured so as to protect at least the effective reflection surface 45 which effectively performs reflection in the octagonal photographing range displayed in the monitor screen 5a of the monitor 5 at the time of photographing.

As a result, in the configuration of the distal end portion 8 of the electronic endoscope 2 according to the present embodiment, the protection member 33 is surface-joined to the reflection surface 48 so that at least the effective reflection surface 45 of the prism 32, which performs refraction in the photographing range displayed in the monitor screen 5a of the monitor 5, is prevented from being exposed. Thus, at the time of assembling, maintenance, and the like, of the image pickup unit 30, it is possible to prevent the effective reflection surface 45 covered with the protection member from being brought into direct contact with the other components, and thereby possible to prevent the effective reflection surface 45 from being flawed or damaged.

According to the present invention as described above, in an electronic endoscope including an optical component for refracting and reflecting photographing light, it is possible to improve the assembling property of an image pickup unit including the optical component, and possible to realize an image pickup unit capable of preventing the optical component from being damaged even in various environment.

The present invention described in the above embodiments is not limited to the embodiments and modifications, and various modifications are possible in an implementation stage within the scope and spirit of the present invention. Further, various stages of the present invention are included in the above described embodiments, and various inventions may be extracted by properly combining the plurality of disclosed constitution elements.

For example, even when several constitution elements are eliminated from all the constitution elements as shown in the embodiments, if it is possible to solve the above described problem and when an effect as described as the effect of the present invention is obtained, the configuration in which the constitution elements are eliminated may also be extracted as the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image pickup unit including a protection member and an optical reflection member, the image pickup unit comprising:
    the optical reflection member which refracts and reflects photographing light introduced from a front surface, by a reflection surface;
    a solid-state image pickup device which has a light receiving portion for receiving the refracted and reflected photographing light;
    the protection member configured to be surface-joined to and to protect at least an area of an effective reflection surface within the reflection surface by which the photographing light is refracted to be made incident on the light receiving portion; and
    a holding frame configured to include therein and hold the optical reflection member and the protection member;
    wherein the optical reflection member and the protection member have tapered surfaces formed by cutting corner portions of one side or both sides of the members, which portions are away from the solid-state image pickup device about an optical axis of the photographing light; and
    the holding frame has inner surfaces facing the tapered surfaces in parallel.

2. The image pickup unit including the protection member and the optical reflection member according to claim 1, wherein the protection member has the same shape as an outer peripheral shape of the optical reflection member about the optical axis of the photographing light.

3. The image pickup unit including the protection member and the optical reflection member according to claim 1,
    wherein the protection member has an outer peripheral shape which is larger than the outer peripheral shape on the upper and lower sides and the both sides of the optical reflection member and which is smaller than the inner surface shape of the holding frame about the optical axis of the photographing light.

4. The image pickup unit including the protection member and the optical reflection member according to claim 1, wherein the protection member includes a joining surface with the optical reflection member, which joining surface has an area smaller than the area of the reflection surface.

5. The image pickup unit including the protection member and the optical reflection member according to claim 1, wherein the protection member is formed of a material having a thermal expansion coefficient substantially the same as the thermal expansion coefficient of the optical reflection member.

6. The image pickup unit including the protection member and the optical reflection member according to claim 5, wherein the protection member is formed of the same glass material as the optical reflection member.

7. The image pickup unit including the protection member and the optical reflection member according to claim 1, wherein the optical reflection member and the protection member are formed of a material having a thermal expansion coefficient substantially the same as the thermal expansion coefficient of the solid-state image pickup device.

8. The image pickup unit including the protection member and the optical reflection member according to claim 7, wherein the protection member is formed of the same glass material as the optical reflection member.

9. The image pickup unit including the protection member and the optical reflection member according to claim 1, wherein the protection member is formed of a light transmissive material and is fixed to the optical reflection member with an ultraviolet curing adhesive, or an ultraviolet curing and thermosetting adhesive.

10. The image pickup unit including the protection member and the optical reflection member according to claim 1, wherein the protection member is joined to the optical reflection member to have a gap of a predetermined distance from the joining surface between the optical reflection member and the solid-state image pickup device.

11. The image pickup unit including the protection member and the optical reflection member according to claim 1, wherein the protection member includes a surface which is in parallel with the joining surface of the optical reflection member which surface is joined to the solid-state image pickup device.

12. The image pickup unit including the protection member and the optical reflection member according to claim 1, wherein the protection member includes a surface which is in parallel with a front surface on the side of an object point, on which front surface the photographing light is made incident.

13. The image pickup unit including the protection member and the optical reflection member according to claim 1, wherein the inner surfaces of the holding frame are away from outer peripheral surfaces of the optical reflection member and the protection member by a predetermined distance.

* * * * *